United States Patent [19]

Stiffey et al.

[11] Patent Number: 4,689,305
[45] Date of Patent: Aug. 25, 1987

[54] SOLID-STATE PHOTOMETER CIRCUIT

[75] Inventors: Arthur V. Stiffey, Slidell, La.; David L. Blank, Arlington, Va.; George I. Loeb, Bethesda, Md.

[73] Assignee: The United States of America as represented by the Secretary of the Navy, Washington, D.C.

[21] Appl. No.: 844,547

[22] Filed: Mar. 24, 1986

[51] Int. Cl.[4] .............................................. C12M 1/34
[52] U.S. Cl. ..................................... 435/291; 435/808; 422/52; 250/361 C
[58] Field of Search ................... 435/4, 8, 34, 39, 291, 435/801, 808; 356/215, 224, 436; 422/52; 250/576; 250/361 R, 361 C, 369, 461.2, 462.1

[56] References Cited

U.S. PATENT DOCUMENTS

| | | | |
|---|---|---|---|
| 3,797,999 | 3/1974 | Witz et al. | 435/291 X |
| 3,849,653 | 11/1974 | Sakaide et al. | 435/291 X |
| 4,303,410 | 12/1981 | Copeland | 422/52 X |
| 4,385,113 | 5/1983 | Chappelle et al. | 435/291 X |
| 4,472,352 | 9/1984 | Quesneau et al. | 435/291 X |
| 4,563,331 | 1/1986 | Losee et al. | 435/291 X |

Primary Examiner—Margaret A. Focarino
Attorney, Agent, or Firm—Thomas M. Phillips

[57] ABSTRACT

A stable, inexpensive and easily constructed photometer consisting of a commercial intergrated photodetection assembly, complementary solid-state operational amplifiers and a solid-state power supply for use in the detection and quantification of low level light emissions from bioluminescence organisms and for the detection of the absence of bioluminescence. Means are provided for controlling the sensitivity of the system as well as providing for direct readout or intergration of the detected signals where they are intermittent.

1 Claim, 1 Drawing Figure

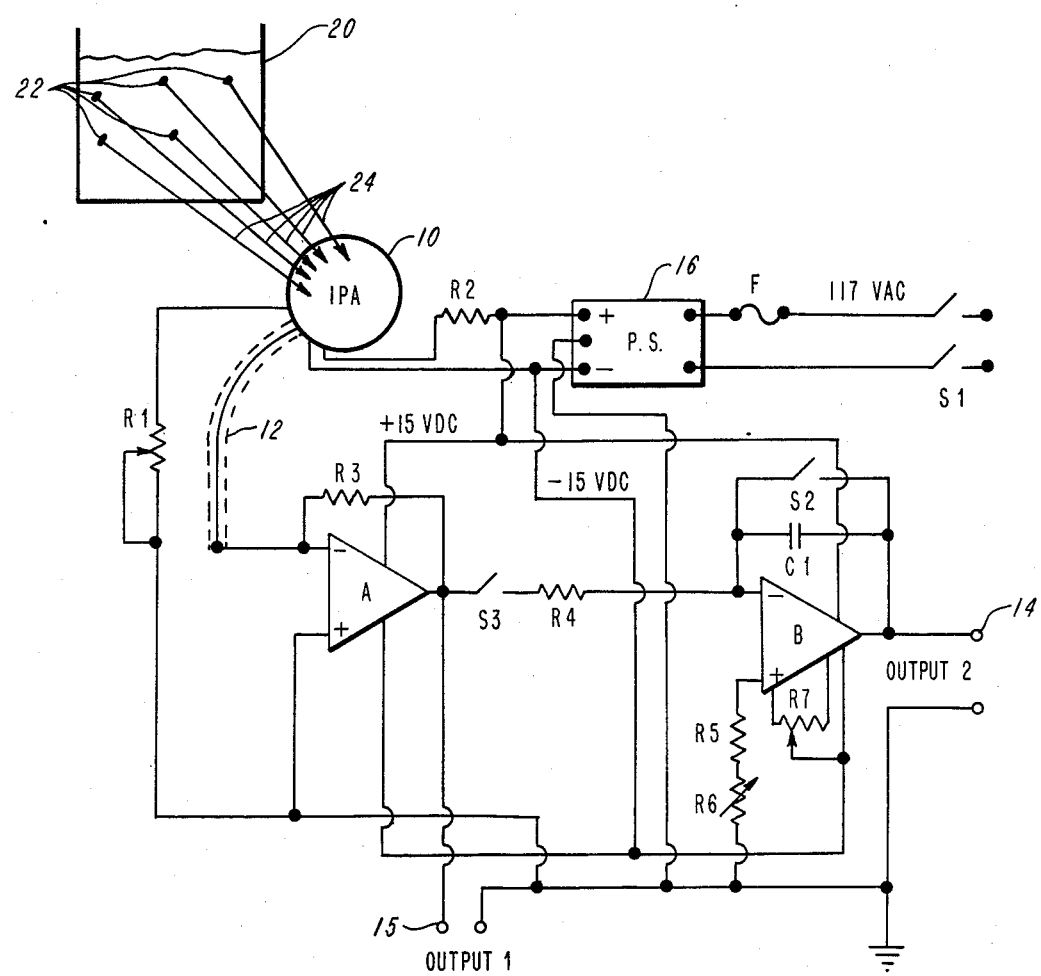

SOLID-STATE PHOTOMETER CIRCUIT

BACKGROUND OF THE INVENTION

1. Field of the Invention

The present invention relates to photometer circuits for studying luminescence and more particularly to photo circuits for studying luminescence wherein luminescence may be continuous or intermittent from dinoflagellates.

2. Description of the Prior Art

Bioluminescence has been the subject of much research, and measurement of this phenomenon has usually been by a photomultiplier photometer originally designed by McNichols in 1952 described in Methods Biochem. Anal. 8, 61, and subsequently modified by Mitchell and Hastings, Strickland and others as described in "A Practical Handbook of Seawater Analysis", second edition bulletin 167, Fisheries Research Board of Canada, Ottawa. There are many commercially designed photometers that are adequate but are expensive.

SUMMARY OF THE INVENTION

The present invention provides for a stable, inexpensive and easily constructed photometer consisting of a commercial integrated photodetection assembly, complementary solid-state operational amplifiers and a solid-state power supply for use in the detection and quanitification of low level light emissions from bioluminescence organisms and for the detection of the absence of bioluminescence. Means are provided for controlling the sensitivity of the system as well as providing for direct readout or integration of the detected signals where they are intermittent.

Accordingly an object of the invention is the provision of an inexpensive and easily constructed photometer for the detection and quantification of low level light emissions from bioluminescence organisms.

Other objects, advantages and novel features of the invention will become apparent from the following detailed description of the invention when considered in conjunction with the accompanying drawing wherein:

BRIEF DESCRIPTION OF THE DRAWING

The single FIGURE of drawing shows a block diagram of a preferred embodiment of the invention.

DESCRIPTION OF THE PREFERRED EMBODIMENT

Referring now the drawing wherein there is shown an integrated photodetection assembly (IPA) 10 which may be by way of example and RCA type 931B photomultiplier tube and intergral solid-state high voltage power supply, voltage regulator and resistor divider network mounted inside an electrostatic shield. The output signal from IPA 10 is fed through a shielded cable 12 to the negative input of a current to voltage convertor A that inverts the polarity of the signal. The output signal from amplifier A is connected through switch S3 and resistor R4 to the negative input of operational amplifier B that is configured (capacitor C1) as an integrating circuit. For the integrated circuit:

$$V_o = -1/RC \int V_A dt$$

where $V_A$ is the output at terminal 14.

offset nul adjustment is provided by a nulling potentometer R7 whose funcion is to zero the output and eliminate drift in the recording instrumentation. Biasing of the integrated circuit is provided by means of a fixed resistor R5 in series with a variable resistor R6.

When measurement of light intensity without integration is desired switch S3 is opened providing an output at terminal 15.

Power from a 117 v source is fed through switch S1 to a supply 16 which provides a $+15$ volt and $-15$ volt to IPA 10.

In operation and by way of example, a small container such as a glass vial 20 containing water in which dinoflagellates 22 are suspended is positioned with respect to the opening in the IPA detector tube so that light 24 emitted by dinoflagellates when agitated will be detected and provide an output current proportional to the light detected.

Measurement of light intensity without integration where, for example, biluminuous bacteria which have continuous light emission, is provided at output 1. Light intensity with integration, for example, dinoflagellates which have intermittent light emission, is obtained by closing switch S3 and provides an output signal at output 2. A shorting switch, S2 is inserted in the circuit to reset the integrator to zero before each determination.

Obviously many modifications and variations of the present invention are possible in light of the above teachings. It is therefore to be understood that within the scope of the appended claims the invention may be practiced otherwise than as specifically described.

We claim:

1. A photometer circuit comprising in combination:
a source of bioluminescence emission;
an integrated photo detection assembly for detecting said bioluminescence emission and providing an output current proportional thereto:
a first operational amplifier configured as a current to voltage converter having a negative input, a positive input and an output;
a second operation amplifier configured as an integrating circuit having a negative input, a positive input and an output;
circuit means connecting the output of said integrated photo detection assembly to the negative input of said first operational amplifier;
a first switch having an opened position and a closed position for connecting the output of said first operational amplifier to the negative input of said second operational amplifier when said first switch is in the closed position;
first and second output terminals
the output of said first operational amplifier being connected to said first output terminal when said first switch is in the open position; and
the output of said second operational amplifier being connected to said second output terminal and providing an output proportional to the total emission of said source of bioluminescence emission when said first switch is in the closed position.

* * * * *